US012336779B2

(12) United States Patent
Ghosh et al.

(10) Patent No.: US 12,336,779 B2
(45) Date of Patent: Jun. 24, 2025

(54) METHOD FOR LOCOMOTION OF A NANOROBOT AND IMPLEMENTATIONS THEREOF

(71) Applicant: INDIAN INSTITUTE OF SCIENCE, Karnataka (IN)

(72) Inventors: Ambarish Ghosh, Bangalore (IN); Debayan Dasgupta, Bangalore (IN)

(73) Assignee: INDIAN INSTITUTE OF SCIENCE, Karnataka (IN)

( * ) Notice: Subject to any disclaimer, the term of this patent is extended or adjusted under 35 U.S.C. 154(b) by 470 days.

(21) Appl. No.: 17/631,735

(22) PCT Filed: Jul. 31, 2020

(86) PCT No.: PCT/IN2020/050676
§ 371 (c)(1),
(2) Date: Jan. 31, 2022

(87) PCT Pub. No.: WO2021/019575
PCT Pub. Date: Feb. 4, 2021

(65) Prior Publication Data
US 2022/0273382 A1    Sep. 1, 2022

(30) Foreign Application Priority Data
Aug. 1, 2019    (IN) .............................. 201941031224

(51) Int. Cl.
*A61B 34/00*    (2016.01)
*A61B 17/00*    (2006.01)
*H01F 10/14*    (2006.01)
(52) U.S. Cl.
CPC .............. *A61B 34/72* (2016.02); *A61B 34/73* (2016.02); *H01F 10/14* (2013.01); *A61B 2017/00345* (2013.01)

(58) Field of Classification Search
CPC .................... A61B 34/72; A61B 34/73; A61B 2017/00345; A61B 2017/00411; H01F 10/14; H01F 41/20
See application file for complete search history.

(56) References Cited

U.S. PATENT DOCUMENTS 6,562,316 B1    5/2003    Edwards et al.
2014/0343488 A1*    11/2014    Beckman ............... A61B 17/22
                                                                    604/95.01
(Continued)

FOREIGN PATENT DOCUMENTS

KR    20100137241 A    12/2010
KR    20180116969 A    10/2018
(Continued)

OTHER PUBLICATIONS

Ghosh et al. "Design Consideration for Effective Thermal Management in Mobile Nanotweezers", 2019 International Conference of Manipulation, Automation and Robotics at Small Scales (MARSS), IEEE, Jul. 1, 2019, pp. 1-6, XP033626570, DOI: 10.1109/MARSS.2019.8860942.

(Continued)

*Primary Examiner* — Sihar A Karwan
(74) *Attorney, Agent, or Firm* — Dickinson Wright PLLC

(57) ABSTRACT

The present disclosure relates to a method for locomotion of at least one nanorobot through a biochemical environment. The present disclosure also reveals a method for locomotion of nanorobots for use in drug delivery, delivery of materials for medical imaging and medical diagnosis.

13 Claims, 3 Drawing Sheets

(56) References Cited

U.S. PATENT DOCUMENTS

| | | | | |
|---|---|---|---|---|
| 2015/0243425 A1* | 8/2015 | Martel | ............... | A61B 34/70 |
| | | | | 361/147 |
| 2015/0380140 A1* | 12/2015 | Duan | ............... | H01F 7/0257 |
| | | | | 600/109 |
| 2016/0241121 A1* | 8/2016 | Choi | ............... | G05B 19/19 |
| 2018/0014798 A1* | 1/2018 | Beckman | ............... | A61B 34/73 |
| 2018/0116744 A1* | 5/2018 | Taya | ............... | A61B 34/73 |
| 2018/0280039 A1* | 10/2018 | Sun | ............... | A61B 1/00195 |
| 2020/0131556 A1* | 4/2020 | Zhang | ............... | G01N 33/54333 |
| 2021/0228298 A1* | 7/2021 | Qiu | ............... | A61B 34/73 |

FOREIGN PATENT DOCUMENTS

| | | |
|---|---|---|
| KR | 20190042305 A | 4/2019 |
| WO | 2006125074 A2 | 11/2006 |
| WO | 2019038258 A1 | 2/2019 |

OTHER PUBLICATIONS

Palagi Stefano et al: "Bioinspired Microrobots", Nature Reviews Material, vol. 3, No. 6, May 10, 2018, pp. 113-124, XP036530465, DOI: 10. 1038/S41578-018-0016-9.
Singh et al, Int. J. Mol. Sci., 208, 19(7), 1979.

* cited by examiner (a)          (b)          (c)

METHOD FOR LOCOMOTION OF A NANOROBOT AND IMPLEMENTATIONS THEREOF

FIELD OF INVENTION

The present disclosure relates to the field of nanotechnology. In particular, it relates to the field of nanomedicine.

BACKGROUND OF THE INVENTION

In traditional drug delivery, an oral or intravascular administration of a drug is followed by typical assimilation of the active moiety, which is then transported uniformly throughout the body via the circulatory system, i.e., blood. However, in case of a localized illness, such as cancer that has not progressed to the metastasis stage, an averaged distribution of drugs may not satisfactorily tackle the illness. Often, an overcompensated dosage regime may sometimes be prescribed in order to ensure delivery of an effective amount to said site. However, as in the case of chemotherapy, the prescribed drugs have severe side-effects and a higher dosage of said drugs is also detrimental to the health of patients.

Owing to the complexity of human anatomy, a number of hurdles need to be overcome in order to successfully implement a drug delivery system. Targeted drug delivery is, therefore, a challenge being faced by researchers worldwide. Said research has largely been fueled by nanomaterials. It is a small size and high surface area of the nanomaterials that allow access to the most seemingly inaccessible parts of human anatomy. For instance, U.S. Pat. No. 6,562,316 reveals a liposomal carrier-based delivery system, wherein the drug enclosed in the lipid carrier is delivered at the required site via the circulatory system. In this case, a careful selection of liposomes is done to ensure ample stability and circulation time. However, such a passive delivery system is reliant on the stability of the carrier system and therefore, an active delivery system wherein suitable navigation is used to deliver the drug is preferred.

WO2006125074 provides a dosage formulation containing magnetic material. Herein, the method of delivery includes orally administering the formulation and applying an extracorporeal magnet to a site on the outside surface of the patient's body in an area that closely apposes the location in the gastrointestinal tract to which delivery of the formulation is desired. Such delivery systems have commonly relied upon the circulatory systems and available body cavities (peritoneal cavity for example) for navigation.

However, movement of active particles/drug through the biochemical environment (such as tissue) has been a challenge due to the presence of dense biopolymer networks, charged proteins, existence of lipophilic and hydrophilic membranes among other things. Therefore, there is a need for a delivery system that allows transport even through a dense biochemical environment.

SUMMARY OF THE INVENTION

In an aspect of the present disclosure, there is provided a method for locomotion of at least one nanorobot through a biochemical environment, the method comprising: a) introducing the at least one nanorobot in the biochemical environment; b) inducing propulsion in the at least one nanorobot in the biochemical environment by applying a magnetic field; and c) heating a localized environment around the at least one nanorobot in the biochemical environment to induce deadhesion and locomotion to the at least one nanorobot.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

DETAILED DESCRIPTION OF THE INVENTION

Figure 1:
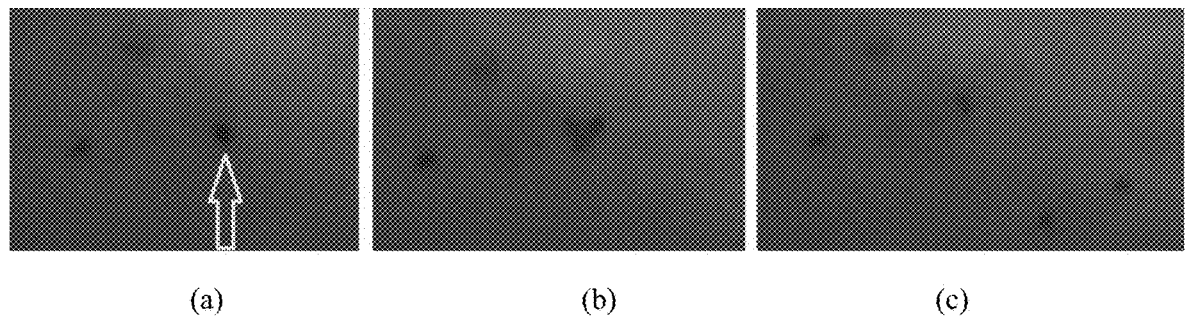
FIG. 1(a-c) illustrates microscopic images of nanorobot in a biochemical environment, in accordance with an embodiment of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a concentration range of about 10-20% should be interpreted to include not only the explicitly recited limits of about 10% to about 20%, but also to include sub-ranges, such as 10%, 12%, 19%, and so forth, as well as individual amounts, including fractional amounts, within the specified ranges, such as 10.5%, and 19.7%, for example.

The term "nanorobot" refers to particles of size ranging from a few tens of nanometers to hundreds of microns having suitable geometry that can show remote or tethered maneuverability while being driven by a wide range of energy source, some of which may be chemical, acoustic, optical, magnetic or some combination of them all. In the present disclosure, the nanorobots are also defined as helical shaped nanoparticles that are small enough to navigate in the biochemical environment. Silica can be used to attain the helical shaped nanorobots and various ferromagnetic materials such as iron, cobalt, nickel, gold, silver or their combinations are used to coat a magnetic layer on the nanorobot. For optically induced heating, plasmonic materials like gold or silver may also be used.

The term "biochemical environment" refers to a media comprising a dense network of biopolymer, whereby the movement of a nanorobot is hampered/restricted. The biochemical environment is an environment selected from at least one fluid, at least one solution, a tissue, an organ, a gel, biological matter, a suspension, a cell, a cell culture, a plant, an animal, a human, soil, a solid, or combinations thereof. The biochemical environment may comprise biopolymers such as collagen, gelatin, hydrogels, extracellular matrix, fibrillar protein, or a mixture of all those among other things.

The term "deadhesion" refers to the detachment of a cell from a surface to which it was adhering. In the present disclosure, deadhesion refers to the unsticking of the nanorobot from the tissues of the biochemical environment. Deadhesion is essential since this propels the locomotion of the nanorobot.

The term "porosity" refers to a measure of the void spaces/pores in a material and is a fraction of the volume of voids over the total volume, between 0 and 1, or as a percentage between 0% and 100%. In the present disclosure, porosity refers to voids/spaces in the biochemical environment. The porosity of the biochemical environment gets expanded or enhanced upon contact with the hot nanorobot. Hence heating the localized environment around the nanorobot results in the enhancement of porosity in the biochemical environment in the range of 10-20% in comparison to the unheated nanorobot. This enhancement in the porosity induces the locomotion of the nanorobot.

The term "IR heating" refers to "Infrared heating" which works by providing electromagnetic radiation with wavelengths between 780 nm and 1 mm for heating a material. The term "magnetic hyperthermia" refers to the heat generated due to the alternate magnetic field, the applied magnetic field converts electromagnetic radiation into heat and thereby induces heat. The term "eddy current heating" refers to the induction heating. The material to be heated is placed within a high frequency current carrying coil. By doing so alternating magnetic field is set up, eddy currents are induced, and the material is heated. The term "radio frequency heating" refers to the process of heating materials through the application of radio waves of high frequency (above 70,000 hertz). In the present disclosure, IR heating or magnetic hyperthermia or eddy current heating or radio frequency heating can be used for heating the localized environment of the nanorobot.

The term "Reynolds number" refers to a dimensionless number which is the ratio of inertial forces to viscous forces of a fluid. In the present disclosure, Reynolds number of the biochemical environment is less than 1.

The term "hydrogels" refers to a network of polymer chains that are hydrophilic, as a colloidal gel in which water is the dispersion medium. In the present disclosure, the term hydrogels refer to a polymeric network such as collagen, gelatin that exists naturally. The term "extracellular matrix" refers to non-cellular component present within all tissues and organs, and provides essential physical scaffolding for the cellular constituents, initiates crucial biochemical and biomechanical cues that a for tissue morphogenesis. The term "fibrillar protein" refers to an insoluble protein that makes up the principal structural proteins of the body. In the present disclosure, the biochemical environment is an environment comprising collagen, gelatin, hydrogels, extracellular matrix, fibrillar protein and combinations thereof.

The term "localized environment" refers to the immediate surrounding around the nanorobot and typically is made up of the biochemical environment into which the nanorobot has been introduced. Assuming the nanorobot to be the center, the heating is targeted on the nanorobot such that heating is localized to a radius within a radius of 1-10 μm. Said heating is noted to selectively heat the nanorobot, which in turn is noted to establish locomotion. However, the locomotion of nanorobot is submitted to be via the contact of "hot" nanorobot and not by the direct heating of the localized environment. Further explanation in this regard has been provided in the example section.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific implementations described herein, which are intended for the purposes of exemplification only. Functionally-equivalent products, compositions, and methods are clearly within the scope of the disclosure, as described herein.

As discussed in the background section, there is a need for targeted drug delivery systems that are capable of navigating through dense biochemical environments such as collagen. Nanocarriers/nanorobots are typically noted to become stuck in such dense media/environment. In this regard, the present disclosure provides a method for locomotion of a nanorobot that has been introduced into a dense biochemical environment. It specifically suggests the application of localized heat to ensure locomotion of a nanorobot that has gotten stuck in said environment.

In an embodiment of the present disclosure, there is provided a method for locomotion of at least one nanorobot through a biochemical environment, the method comprising: a) introducing the at least one nanorobot in the biochemical environment; b) inducing propulsion in the at least one nanorobot in the biochemical environment by applying a magnetic field; and c) heating a localized environment around the at least one nanorobot in the biochemical environment to induce deadhesion and locomotion to the at least one nanorobot. In another embodiment of the present disclosure, step c) involves heating the nanorobot in the biochemical environment to induce deadhesion and locomotion.

In an embodiment of the present disclosure there is provided a method for locomotion of at least one nanorobot through a biochemical environment as described herein, wherein the at least one nanorobot is in helical structure formed by deposition of silica further coated with iron, cobalt, nickel, gold, silver and combinations thereof. In another embodiment of the present disclosure, wherein the at least one nanorobot is in helical structure formed by deposition of silica further coated with iron films and silver films. In yet another embodiment of the present disclosure wherein the iron films are in the range of 30 nm to 60 nm and wherein the silver films are in the range of 10 nm to 30 nm.

In an embodiment of the present disclosure, there is provided a method for locomotion of at least one nanorobot through a biochemical environment as described herein, wherein the heating is localized to a radius of 1-10 μm around the at least one nanorobot in the biochemical environment. In another embodiment of the present disclosure, the heating is localized to a radius of 4.5-5.5 μm around the at least one nanorobot in the biochemical environment. In yet another embodiment of the present disclosure, the heating is effective in increasing the temperature of the nanorobot selectively.

In an embodiment of the present disclosure, there is provided a method for locomotion of at least one nanorobot through a biochemical environment as described herein, wherein heating the localized environment around the at least one nanorobot in the biochemical environment enhances porosity to induce locomotion to the at least one nanorobot. In another embodiment of the present disclosure, the enhancement in porosity may be induced by the contact with heated nanorobot.

In an embodiment of the present disclosure, there is provided a method for locomotion of at least one nanorobot through a biochemical environment as described herein, wherein the enhancement in porosity is in the range of 10-20%. In another embodiment of the present disclosure, the enhancement in porosity is in the range of 11-19%.

In an embodiment of the present disclosure, there is provided a method for locomotion of at least one nanorobot through a biochemical environment as described herein, wherein the heating the localized environment is carried out by a process selected from IR heating, magnetic hyperthermia, eddy current heating, radio frequency heating, or combinations thereof. In another embodiment of the present disclosure, the heating is carried out by laser induced IR heating. In another embodiment of the present disclosure, the heating is targeted heating which heats the nanorobot and has minimal effect on the surrounding biochemical environment. In yet another embodiment of the present disclosure, the heating is carried out by magnetic hyperthermia. In one another embodiment of the present disclosure, wherein the heating allows the nanorobots to get unadhered in the biochemical environment.

In an embodiment of the present disclosure, there is provided a method for locomotion of at least one nanorobot through a biochemical environment as described herein, wherein the application of a magnetic field is selected from at least one of a homogenous magnetic field, a time-varying magnetic field, a magnetic field that changes its direction, a magnetic field that rotates, and a magnetic field that contains a gradient, and combinations thereof. In another embodiment of the present disclosure, the application of the magnetic field is a time-varying magnetic field. In another embodiment of the present disclosure, the magnetic hyperthermia is carried out by application of a magnetic field having a strength in the range of $1\times10^3$-$3\times10^4$ G oscillating at a frequency of 10-500 kHz. In another embodiment of the present disclosure, the application of a magnetic field has a strength in the range of $5\times10^3$-$2.8\times10^4$ G oscillating at a frequency of 50-480 kHz.

In an embodiment of the present disclosure, there is provided a method for locomotion of at least one nanorobot through a biochemical environment as described herein, wherein the application of a magnetic field has a strength in the range of 80-160 G. In another embodiment of the present disclosure, wherein the application of a magnetic field that rotates has a strength of 150 G. In yet another embodiment of the present disclosure, the magnetic field has a strength of 100 G.

In an embodiment of the present disclosure, there is provided a method for locomotion of at least one nanorobot through a biochemical environment as described herein, wherein the biochemical environment is an environment comprising collagen, gelatin, hydrogels, extracellular matrix, fibrillar protein, and combinations thereof.

In an embodiment of the present disclosure, there is provided a method for locomotion of at least one nanorobot through a biochemical environment as described herein, wherein the biochemical environment has a reynolds number less than 1.

In an embodiment of the present disclosure, there is provided a method for locomotion of at least one nanorobot through a biochemical environment as described herein, wherein the biochemical environment is an environment comprising collagen, gelatin, hydrogels, extracellular matrix, fibrillar protein, and combinations thereof and the biochemical environment has a Reynolds number less than 1.

In an embodiment of the present disclosure, there is provided a method for locomotion of at least one nanorobot through a biochemical environment as described herein, wherein the biochemical environment has a viscosity in the range of 0.5 cP to $1\times10^6$ cP. In another embodiment of the present disclosure, the biochemical environment has a viscosity in the range of 0.8 cP to $1\times10^5$ cP.

In an embodiment of the present disclosure, there is provided a method for locomotion of at least one nanorobot through a biochemical environment as described herein, wherein the biochemical environment is an environment comprising collagen, gelatin, hydrogels, extracellular matrix, fibrillar protein, and combinations thereof and the biochemical environment has a viscosity in the range of 0.5 cP to $1 \times 10^6$ cP.

In an embodiment of the present disclosure, there is provided a method for locomotion of at least one nanorobot through a biochemical environment as described herein, wherein the at least one nanorobot has an inner hull to carry a cargo of actives like anti-cancer drugs, radioactive agent for imaging, radioisotopes for radiotherapy and drugs for chemotherapy.

In an embodiment of the present disclosure, there is provided a method for locomotion of at least one nanorobot through a biochemical environment as described herein, wherein the biochemical environment is an environment comprising collagen, gelatin, hydrogels, extracellular matrix, fibrillar protein, and combinations thereof and the biochemical environment has a viscosity in the range of 0.5 cP to $1 \times 10^6$ cP and the at least one nanorobot has an inner hull to carry a cargo of actives like anti-cancer drugs, radioactive agent for imaging, radioisotopes for radiotherapy and drugs for chemotherapy.

In an embodiment of the present disclosure, there is provided a method for locomotion of at least one nanorobot through a biochemical environment as described herein, wherein the method is used for delivery of the drug molecules. In another embodiment of the present disclosure, the drug molecule is doxorubicin.

In an embodiment of the present disclosure, there is provided a method for locomotion of at least one nanorobot through a biochemical environment as described herein, wherein the method is used as a contrast agent in medical imaging. In another embodiment of the present disclosure, the contrast agent is employed to image tumors.

In an embodiment of the present disclosure, there is provided a method for locomotion of at least one nanorobot through a biochemical environment as described herein, wherein the method is used to deliver materials that aid medical diagnosis.

In an embodiment of the present disclosure, there is provided a method for locomotion of at least one nanorobot through a biochemical environment as described herein, wherein the method is used to deliver material that has therapeutic value. Therapeutic value is defined as the ability of a material, i.e., substance/drug to treat an illness or restrict the symptoms. Substances having therapeutic value include substances having improved bioavailability.

In an embodiment of the present disclosure, there is provided a method for locomotion of at least one nanorobot through a biochemical environment, the method comprising:
a) introducing the at least one nanorobot in the biochemical environment comprising collagen, gelatin, hydrogels, extracellular matrix, fibrillar protein, and combinations thereof;
b) inducing propulsion in the at least one nanorobot in the biochemical environment by applying a magnetic field selected from at least one of a homogenous magnetic field, a time-varying magnetic field, a magnetic field that changes its direction, a magnetic field that rotates, a magnetic field that contains a gradient, or combinations thereof having a strength in the range of 80-160 G; and c) heating a localized environment by a process selected from IR heating, magnetic hyperthermia, eddy current heating, radio frequency heating, or combinations thereof around the at least one nanorobot in the biochemical environment to induce deadhesion and locomotion to the at least one nanorobot, wherein the biochemical environment has a reynolds number less than 1 and wherein the biochemical environment has a viscosity in the range of 0.5 cP-$1 \times 10^6$ cP.

In an embodiment of the present disclosure, there is provided a method for locomotion of at least one nanorobot through a biochemical environment, the method comprising:
a) introducing the at least one nanorobot in the biochemical environment comprising collagen, gelatin, hydrogels, extracellular matrix, fibrillar protein, and combinations thereof;
b) inducing propulsion in the at least one nanorobot in the biochemical environment by applying a magnetic field that rotates, having a strength in the range of 100-150 G; and c) heating a localized environment by a process selected from IR heating, or magnetic hyperthermia having a strength in the range of $1 \times 10^3$-$3 \times 10^4$ G oscillating at a frequency of 10-500 kHz around the at least one nanorobot in the biochemical environment to induce locomotion to the at least one nanorobot, wherein the biochemical environment has a reynolds number less than 1 and wherein the biochemical environment has a viscosity in the range of 0.5 cP-$1 \times 10^6$ cP.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

Nanoparticles are preferred models for carrying out passive drug delivery. For instance, nanoparticles owing to their small sizes are known to easily get accumulated in tumor cells which have porous cell membranes (Singh et al, Int. J. Mol. Sci., 208, 19(7), 1979). However, as mentioned above, targeted delivery (or active delivery) through a biochemically dense network is a challenge. Herein, not only is the relative density of biological tissue a problem, added complications include the presence of charged proteins that can potentially hinder the movement of nanoparticles and also presence of lipophilic/lipophobic membrane barriers. The present disclosure attempts to address the problem by presenting a method of locomotion. The examples below will describe the method for locomotion of at least one nanorobot through a biochemical environment.

Materials and Methods

Figure 3:
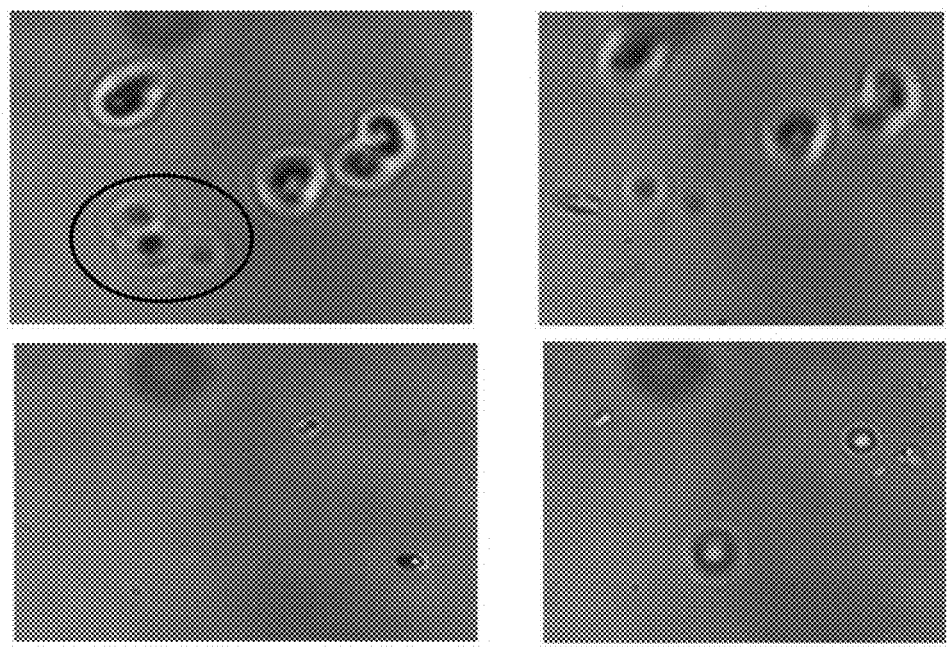
FIG. 3 illustrates microscopic images of nanorobot in a biochemical environment, in accordance with an embodiment of the present disclosure.

A tissue, represented here by a chicken tissue, was procured from the local market. (3-Amino)triethoxysilane (APTES) used to coat the glass slide and 1H1H2H2H-perfluorooctyltriethoxysilane (PFO) used to coat the nanorobot as shown in FIG. 3 was procured from Sigma-Aldrich.

Example 1

Method for Locomotion of at Least One Nanorobot Through a Biochemical Environment The possibility of locomotion of a magnetically-controlled nanorobot through a dense biochemical environment such as tissue was tested by using a chicken muscle, in which iron coated nanorobot was injected/introduced. These nanorobots were helical in structure and were created by the Glancing Angle Deposition of silica on seed layers. A thin film of silver (~10 nm) and a film of iron (~45 nm) were coated on these helices. The application of strong magnetic field (100 G) was found to have no effect on the nanorobot, indicating that the nanorobot was completely stuck in the collagenous environment (Reynolds number <1 and a viscosity in the range of 0.5 cP to $10^6$ cP). Subsequently, a defocused IR laser beam (1064 nm) was used to heat the surface of the nanorobot, which was found to induce deadhesion or un-sticking, thereby inducing locomotion (refer FIG. 1a) under the influence of the magnetic field. The power of beam was calculated to be 54 mW having an incident area of 5 μm (localized environment around the nanorobot). The middle panel of FIG. 1(b) shows slight movement of the nanorobot from its initial position as shown in the first panel. The track created during the motion is also visible. In the third panel FIG. 1c the nanorobots are seen to have moved further away. Alternatively, magnetic hyperthermia could be initiated to induce locomotion ($1\times10^3$-$3\times10^4$ G 500 kHz).

The heating of the localized environment was found to lead to selective heating of the nanorobot. The "hot" nanorobot was found to regain locomotion, as evidenced by the "tracks" observed in the middle panel of FIG. 1. This was also accompanied with formation of bubbles. Although, formation of bubble was not considered necessary for locomotion, its formation along with tracks created during motion was considered as evidence to prove the un-sticking of the nanorobot.

Further, no "bubbles" were observed when the beam was incident on an area devoid of the nanorobot, thus indicating that the "hot" nanorobot was influential in inducing locomotion.

Figure 2:
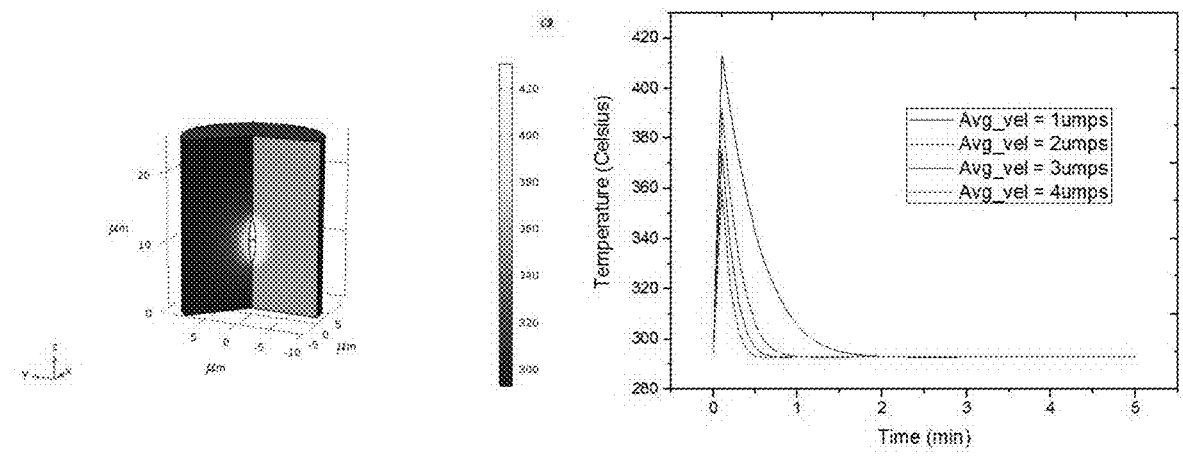
FIG. 2 illustrates simulated spectrum of transient heating of the nanorobot in a biochemical environment, in accordance with an embodiment of the present disclosure.

In order to map the effect of heating a nanorobot, a simulation of the transient heating of a 3 μm ellipsoid subjected to a flow of water comparable to the nanorobots velocity was done using COMSOL. The transient analysis of the way the flowing water removes heat from the ellipsoid identifies the time necessary before ellipsoid to return to room temperature. The simulation geometry and the resulting heat loss curve are shown in FIG. 2. The transient analysis of the way the flowing water removes heat from the ellipsoid is used to predict the amount of time the nanorobot will be heated enough to execute motion.

In order to test the validity of the mentioned simulation, i.e., the un-sticking was indeed due to heat, the nanorobots were coated with Perfluorooctanesulfonic acid (PFOS) to give them a negative charge. Said particles were then drop-cast on a (3-Amino)triethoxysilane (APTES) coated glass slide. The APTES was used to mimic a condition of strong adhesion. The glass slide was observed under the microscope at 50× magnification (refer FIG. 3). Initially, the nanorobots were identified to be stuck, despite presence of magnetic field (100 G). Upon heating (54 mW beam incident on a 5 micron diameter), the nanorobots were observed to de-adhered and propel (under the applied magnetic field) to the surface. The heating was provided in short bursts, just enough to visually confirm the unsticking of nanorobots (refer FIG. 3). It was observed, that the period of locomotion, before the nanorobot became stuck again was found to be approximately 10 seconds. Therefore, in an in vivo scenario, one can envisage moving the nanorobots for some duration till they become stuck, and then turning the heat on for a short duration to de-adhere the stuck nanorobots allowing them to resume motion.

Figure 4:
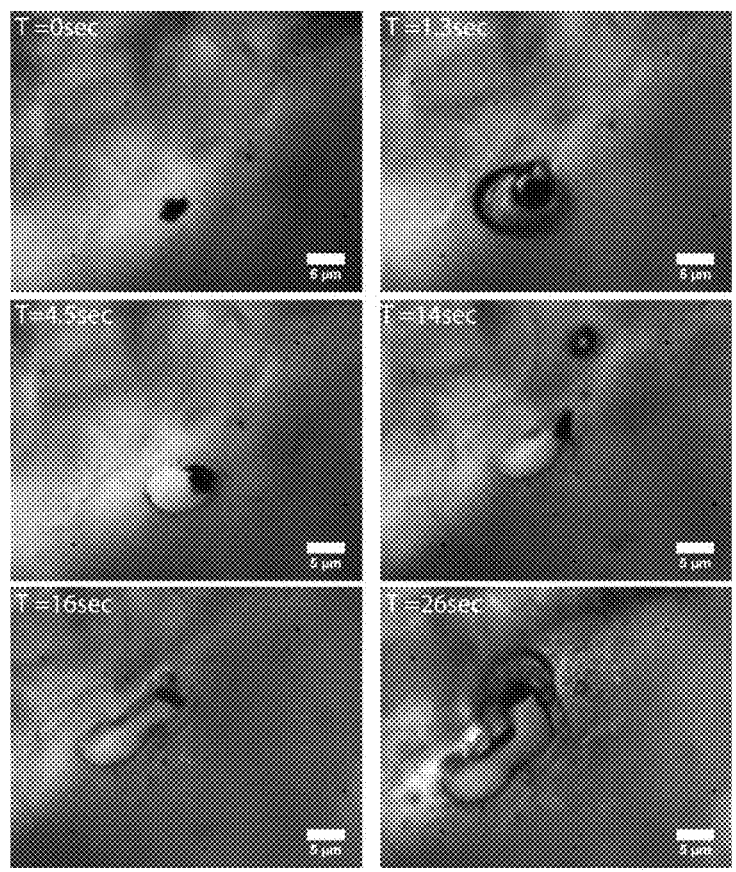
FIG. 4 illustrates sequential microscopic images of nanorobot in a biochemical environment, in accordance with an embodiment of the present disclosure.

Without being bound by theory, it is hypothesized that localized heating by hot nanorobots can achieve propulsion through the live tissue by making tiny pathways of denatured polymer chains and simultaneously overcoming the hindrance from charged networks. Additionally experiments were performed to understand the contributing factors for the heat induced motion. The tissue injected with the nanorobot was subjected to laser induced heating. FIG. 4 depicts the image sequence from the video captured on the heated nanorobot. The images sequentially captured at various time showed tracks created by the movement of the heated particles through the tissue. These tracks left on the tissue were due to irreversible denaturation of collagen and there occurred local biopolymer degradation. These biopolymer degradation facilitated the mobility of nanorobot upon heating. However, these degradations are microscopic in nature and gets healed in the living systems.

Figure 5:
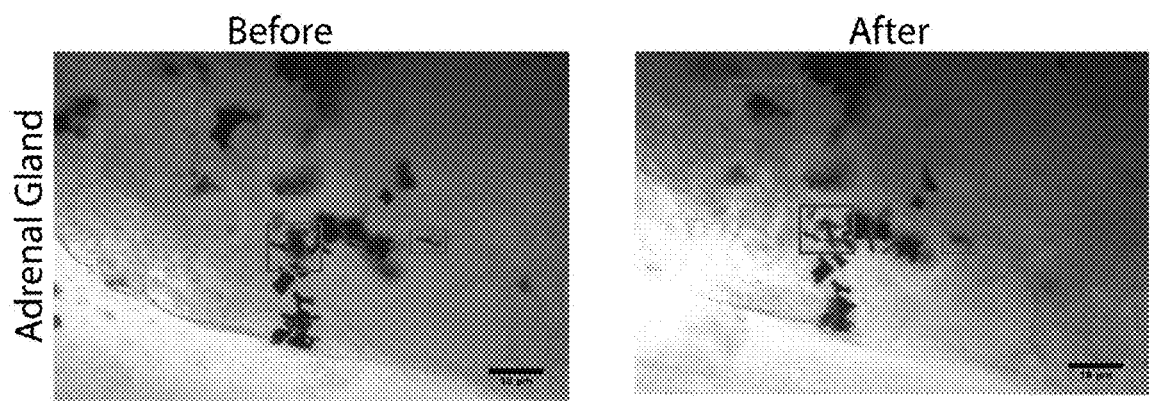
FIG. 5 illustrates microscopic images of nanorobot in a biochemical environment in the presence of a rotating magnetic field, in accordance with an embodiment of the present disclosure.

A magnetic field that rotates i.e. a rotating magnetic field of 150 G was used to induce the mobility of the nanorobot. FIG. 5 represent the images of the displacement of the particles in the tissue after they were subjected to magnetic hyperthermia ($1\times10^4$ G, 300 sec) and rotating field (150 G 3 Hz) simultaneously. The images depicted that the particles had moved into the tissue at the application of the magnetic field. This clearly confirmed that deadhesion and subsequent motion of the nanorobot had occurred due to the localized heating generated by the oscillating magnetic field.

It is important to note that the nanorobots need not be heated by using light only, one can envisage using different forms of hyperthermia such as radio frequency, acoustic, among others.

Example 2

Hyperthermia Induced Apoptosis Using the Nanorobot of the Present Disclosure

The method of the locomotion of the nanorobot in the biochemical environment explained in Example 1 can be used for drug delivery as the nanorobot has an inner hull to carry a cargo of actives like anti-cancer drugs, radioactive agent for imaging, radioisotopes for radiotherapy and drugs for chemotherapy. Further, the 'hot' nanorobots results in the hyperthermia and which in turn induced apoptosis i.e. death of cells. Hence the nanorobots programmed for specific/localized landing in the biochemical environment can result in apoptosis of infective cells and foreign bodies. For example, in the present disclosure hyperthermia induced death of cells have been observed where heat killed bacteria (FIG. 6) and cancer cells (FIG. 7).

Figure 6:
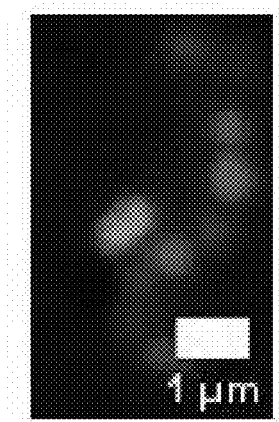
FIG. 6 illustrates images of nanorobot in a biochemical environment post-hyperthermia, in accordance with an embodiment of the present disclosure.
Figure 7:
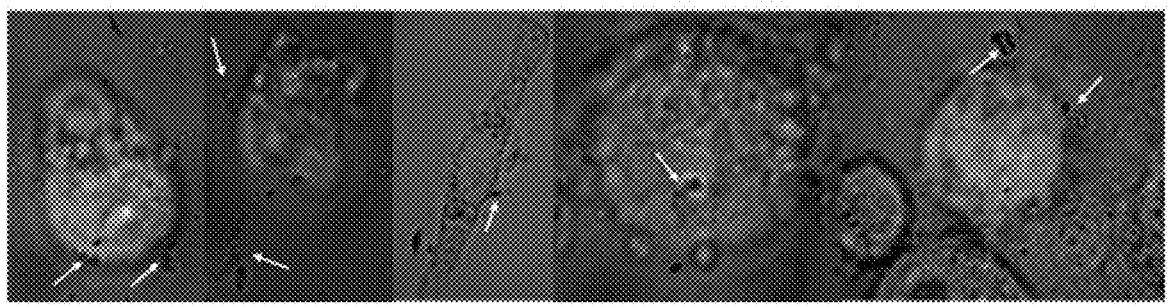
FIG. 7 depicts propidium iodide (PI) stained cancer cells post-hyperthermia, in accordance with an embodiment of the present disclosure.

FIG. 6 depict the image showing a single nanorobot found beside a chain of dead bacterial colony post hyperthermia. In this experiment E. faecalis bacteria in suitable media was mixed with nanorobots in a vial. The vial was subjected to a rotating field (50 G, 10 Hz) to ensure motion of nanorobots so that they get evenly distributed throughout the vial and are placed in the vicinity of bacteria with higher probability. This solution was then placed inside the hyperthermia coil. After magnetic hyperthermia the bacteria-nanorobot solution was treated with Propidium Iodide (PI) which fluoresces red signaling cell death. FIG. 7 depict Propidium Iodide (PI) stained (showing death) cancer cells post-hyperthermia. For this experiment, a glass bottomed dish was seeded with cancer cells. Once the cell culture was prepared, the nanorobots were introduced into the culture by a micro-pipette and then driven towards the cells by rotating magnetic field (50 G, 10 Hz) for 30 minutes. Once it was confirmed under a microscope that nanorobots have reached the cancer cells, the dish was subjected to hyperthermia. The result shown in FIG. 7 is post hyperthermia. The red fluorescent PI signal indicated cell death when the cell is in contact with nanorobots (pointed by white arrows).

Further it is contemplated that the nanorobots can get adhered to the walls of the dentinal tubules in teeth since the naturally occurring fluid in dentinal tubule is a protein rich fluid. This method of deadhesion due to local heat will also be useful for overcoming the adhesion to many physiologically relevant environments, e.g. Haversian canals close to the central bone narrow, dentinal tubule walls, intracellular space in most organ tissues and in general to almost all biological environments.

Although the subject matter has been described in considerable detail with reference to certain examples and implementations thereof, other implementations are also possible.

ADVANTAGES OF THE PRESENT DISCLOSURE

The present disclosure provides method of locomotion of at least one nanorobot through a biochemical environment. The method, in principal utilizes selective heating to re-initiate locomotion (magnetic propulsion) in a nanorobot that has become stuck in a dense biochemical environment. The method, is therefore, highly useful in active drug delivery to sites protected by dense bio-polymeric network such as collagenous tissues. The method is applicable to a wide variety of nanorobots and also diverse environments. Therefore, the method is efficient in terms of preventing investment in terms of identifying specific nanorobots that are capable of penetrating such dense networks (Reynolds number less than 1). The method aids in hyperthermia induced apoptosis (death of cells) and exhibits therapeutic value in destroying bacterial cells and the cancer cells. The present disclosure also provides a method for locomotion of nanorobot for use in drug delivery, delivery for materials for medical diagnosis and imaging.

We claim:
1. A method for locomotion of at least one nanorobot through a biochemical environment, the method comprising:
   (a) introducing the at least one nanorobot in the biochemical environment;
   (b) inducing propulsion in the at least one nanorobot in the biochemical environment by applying a magnetic field of a strength in the range of 80-160 G; and
   (c) heating a localized environment around the at least one nanorobot in the biochemical environment to induce deadhesion and locomotion to the at least one nanorobot,
   wherein the heating the localized environment is carried out by a process selected from IR heating, magnetic hyperthermia carried out by application of a magnetic field having a strength in the range of $1 \times 10^3$ to $3 \times 10^4$ G oscillating at a frequency of 10 to 500 kHz, eddy current heating, radio frequency heating, or combinations thereof.

2. The method as claimed in claim 1, wherein the heating is localized to a radius of 1-10 μm around the at least one nanorobot in the biochemical environment.

3. The method as claimed in claim 1, wherein heating the localized environment around the at least one nanorobot in the biochemical environment enhances porosity to induce locomotion to the at least one nanorobot.

4. The method as claimed in claim 3, wherein the enhancement in porosity is in the range of 10-20%.

5. The method as claimed in claim 1, wherein the application of a magnetic field is selected from at least one of a homogenous magnetic field, a time-varying magnetic field, a magnetic field that changes its direction, a magnetic field that rotates, a magnetic field that contains a gradient, or combinations thereof.

6. The method as claimed in claim 1, wherein the biochemical environment is an environment comprising collagen, gelatin, hydrogels, extracellular matrix, fibrillar protein, and combinations thereof.

7. The method as claimed in claim 6, wherein the biochemical environment has a reynolds number less than 1.

8. The method as claimed in claim 6, wherein the biochemical environment has a viscosity in the range of 0.5 cP-$1 \times 10^6$ cP.

9. The method as claimed in claim 1, wherein the at least one nanorobot has an inner hull to carry a cargo of actives like anti-cancer drugs, radioactive agent for imaging, radioisotopes for radiotherapy and drugs for chemotherapy.

10. The method as claimed in claim 1, wherein the method is used for delivery of the drug molecules.

11. The method as claimed in claim 1, wherein the method is used as a contrast agent in medical imaging.

12. The method as claimed in claim 1, wherein the method is used to deliver materials that aid medical diagnosis.

13. The method as claimed in claim 1, wherein the method is used to deliver material that have therapeutic value.

* * * * *